United States Patent [19]

Vinogradov et al.

[11] Patent Number: 5,002,933

[45] Date of Patent: Mar. 26, 1991

[54] HEXAPEPTIDE AND MEDICINAL PREPARATION PRODUCED FROM IT TO TREAT EROSIVE AND ULCERATIVE LESIONS OF GASTROINTESTINAL TRACT

[76] Inventors: Valentin A. Vinogradov, Khoroshevskoe shosse, 34, kv. 38; Mikhail I. Titov, Osennaya ulitsa, 2, kv. 117; Vladimir M. Polonsky, ulitsa Krasina, 14, kv. 25; Nikolai V. Korobov, Ulitsa Akademika Bochvara, 6, kv. 37, all of, Moscow; Anatoly S. Sokolov, Jubileiny prospekt, 68, kv. 55, Moskovskaya Oblast, Khimki; Maria L. Yakusheva, Vinnitskaya ulitsa, 3, kv. 13, Moscow; Zhanna D. Bespalova, Kuntsevskaya ulitsa, 1/5, kv. 229, Moscow; Mikhail V. Ovchinnikov, ulitsa Ostrovityanova, 16, korpus 3, kv. 26, Moscow; Boris L. Pekelis, pereulok Sivtsev Vrazhek, 21, kv. 36, Moscow, all of U.S.S.R.

[21] Appl. No.: 328,159

[22] PCT Filed: May 25, 1988

[86] PCT No.: PCT/SU88/00115

§ 371 Date: Feb. 3, 1989

§ 102(e) Date: Feb. 3, 1989

[87] PCT Pub. No.: WO88/10268

PCT Pub. Date: Dec. 29, 1988

[30] Foreign Application Priority Data

Jun. 19, 1987 [SU] U.S.S.R. .............................. 4262648

[51] Int. Cl.$^5$ .......................... C07K 7/06; A61K 37/02

[52] U.S. Cl. ...................................... 514/17; 530/329

[58] Field of Search ........................... 530/329; 514/17

[56] References Cited

U.S. PATENT DOCUMENTS

| | | | |
|---|---|---|---|
| 4,457,917 | 7/1984 | Schaller | 424/177 |
| 4,565,805 | 1/1986 | Smirnov et al. | 514/17 |

FOREIGN PATENT DOCUMENTS

| | | | |
|---|---|---|---|
| 0188629 | 4/1985 | European Pat. Off. | 514/17 |
| 0189485 | 4/1985 | European Pat. Off. | 514/17 |
| 0187956 | 12/1985 | European Pat. Off. | 514/19 |
| 2541115 | 12/1983 | France | 514/17 |
| 0661869 | 10/1987 | Switzerland | 514/17 |

OTHER PUBLICATIONS

Allan et al., *Inflammatory Bowel Diseases*, 1983, pp. 126, 218, 233, 418–422.

Somerville et al., *Drugs*, Mar. 1983, 25(3), 315–330.

Polonskii et al., *Chem. Abstracts.*, 1986, 107(3): 18082r.

*Primary Examiner*—Lester L. Lee
*Assistant Examiner*—Stephen B. Maebius
*Attorney, Agent, or Firm*—Burgess, Ryan & Wayne

[57] ABSTRACT

A novel hexapeptide is provided having the following structure:

Tyr-D-Ala-Gly-Phe-Leu-Glu also provided is a proposed medicinal preparation for treatment of erosive and ulcerative lesions of the gastrointestinal tract comprised of an active principle, said hexapeptide, and a pharmaceutical carrier.

5 Claims, No Drawings

HEXAPEPTIDE AND MEDICINAL PREPARATION PRODUCED FROM IT TO TREAT EROSIVE AND ULCERATIVE LESIONS OF GASTROINTESTINAL TRACT

BACKGROUND OF THE INVENTION

1. Field of the Invention

This invention relates to organic chemistry and more particularly it relates to a novel hexapeptide and a novel medicinal preparation to treat erosive and ulcerative lesions of the gastrointestinal tract, based thereon.

2. Prior Art

Antagonists to histamine $H_2$ receptors, e.g. cimetidine, (Somerville K. M., Langman, M. J. S. "Drugs", 1983, 24, p. 315–330) are now widely used (per os) to treat exacerbations of gastric and duodenal ulcer. Said preparations is given as tablets for several months. Short courses of cimetidine therapy usually provoke relapses of peptic ulcer. Administration of cimetidine produces some side effects, such as diarrhea, myalgia, allergic reactions, depressions, gynaecomasty due to hypersecretion of prolactin, inhibition of the intrinsic factor secretion and of vitamin $B_{12}$ absorption, and impairment of the excretory hepatic function. For these consideration cimetidine is not recommended for treatment of patients with hepatic and renal failure and some other diseases.

Patients with ulcerative colitis are now mainly treated with sulfasalazine (a mixture of 5-aminosalicylate and sulfapyridine). It is given orally, but is poorly tolerated by patients, producing side effects such as nausea, vomiting, headache, allergic response and leucopenia ("Inflammatory Bowel Diseases", ed. by R. N. Allan, Edinburg, 1983).

A hexapeptide having the formula Tyr-D-Ala-Gly-Phe-Leu-Arg is known in the prior art. Its structure is similar to that of the proposed new hexapeptide (U.S. Pat. No. 4,565,005), and the preparation is used to treat duodenal ulcer. But the preparation is effective only when given parenterally, while its efficacy with administration per os is low.

SUMMARY OF THE INVENTION

The herein-proposed hexapeptide and a medicinal preparation produced from it are novel and have not been described in the literature.

The object of this invention is to provide a novel hexapeptide and a medicinal preparation produced from this hexapeptide that would have high anti-ulcerative activity without producing side effects.

Said object has been attained due to the fact that, according to the invention, a novel hexapeptide is proposed having the following structure:

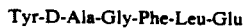

Tyr-D-Ala-Gly-Phe-Leu-Glu

The hexapeptide proposed herein is a white powder, readily soluble in distilled water, physiological saline, alcohol; insoluble in ether, ethyl actate, benzene, or hexane; $[\alpha]_D^{20} = +29.8°$ (1.0 with 1.10% Ac OH); $R_f$: 0.74 (chloroform:methanol:32 percent acetic acid, 60:45:20), 0.42 (ethyl acetate:pyridine:acetic acid:water, 45:20:6:11), 0.48 (n-butyl alcohol:acetic acid:water, 3:1:1): amino acid assay: alanine, 1.02 (I); glycine, 1.00 (I); glutamic acid, 1.04 (I); leucine, 1.02(I); tyrosine, 0.99 (I); phenylalanine, 1.03 (I); findings of high performance liquid chromatography: the peptide was eluted with one peak at 38.24 percent gradient in 12,16 minutes. The column: 250×4.6 mm, Ultresphera ODS 5 m; the mobile phase A: 0.05M $KH_2PO_4$, B: $CH_3CN$; grad 20→50 percent B per 20 min.; pressure, 1500 psi; flow rate, 1 ml/min; detection at 214 nm.

The proposed hexapeptide is potent against ulcer. The medicinal preparation comprising an active principle and a carrier, comprises the proposed hexapeptide as the active principle.

The proposed medicinal preparation can be used in any form suitable for oral administration, e.g. as powder or tablets that can be taken per os with milk, vegetable oil or lipids (in a dispersed form), or in the form of capsules containing any suitable pharmaceutical fat carrier. Besides, the preparation can be given as an intranasal aerosol or as rectal suppositories.

The proposed preparation preferably contains 5–50 mg of the active principle in a single dose. The proposed preparation in the form of capsules contains preferably the active principle in the quantity of 5–50 mg in one capsule, while olive oil is used as a pharmaceutical carrier.

BEST WAY OF CARRYING THE INVENTION INTO EFFECT

The efficacy of the proposed hexapeptide has been studied on experimental animals. Vister male rats were used to compare the therapeutic efficacy of the proposed preparation with that of the known preparations.

Duodenal ulcer was induced in experimental animals by subcutaneous administration of cysteamine hydrochloride in a dose of 350 mg per kg body weight (in 0.5 ml of physiological saline). The proposed preparation was given to the rats immediately and in 6 hours following the administration of the provoking agent. The proposed hexapeptide was given into the stomach through a gastric tube in doses of 10 and 100 mcg/kg; the known hexapeptide (U.S. Pat. No. 4,565,705) was given in a dose of 100 mcg/kg (cimetidine in a dose 10 mg/kg) in 0.5 ml of a 3 percent milk (five-fold diluted in physiological saline). Control animals were given 0.5 ml of a 3 percent milk diluted in a 5-fold volume of physiological saline immediately after administration of cysteamine hydrochloride and 6 hours later. The animals were sacrificed by decapitation in 24 hours after administration of cysteamine hydrochloride and the condition of the duodenal mucosa was assessed in them.

The severity of lesion was determined for each group of the rats using the following scoring system: 0—absense of ulceration; 1—erosion; 2—single ulcer; 3—multiple ulcers; 4—perforating ulcer. Besides, the incidence of lesion was determined in each group: the ratio of the animals with ulcer to the total number of survivals by the end of the experiment was determined. A conventional ulcer index (severity of lesion+doubled incidence of affections) was thus derived as the summary involvement index.

The obtained findings were treated statistically using the Student t-criterion (for severity of lesion) and Pirson $X^2$ criterion (for the incidence). The differences at the level of 95 percent significance were taken as trustworthy ($P < 0.05$). The results of the experiments are illustrated in Table 1.

TABLE 1

Effect of the proposed hexapeptide, cimetidine and the known anti-ulcer hexapeptide on development of cysteamine-induced duodenal ulcer with oral administration of the preparations

| Item | Control group | Proposed hexapeptide, (10 μg/kg) | Proposed hexapeptide (100 μg/kg) | Cimetidine, (10 mg/kg) | Known hexapeptide (100 μg/kg) |
|---|---|---|---|---|---|
| 1 | 2 | 3 | 4 | 5 | 6 |
| Lesion scoring | 2.17 ± 0.15 | 1.60 ± 0.27 | 0.83 ± 0.17* | 1.00 ± 0.26* | 1.62 ± 0.19 |
| Incidence | 0.86 | 0.80 | 0.31* | 0.33* | 0.65 |
| Ulcer index | 3.89 | 3.20 | 1.45 | 1.66 | 2.92 |
| Ulcer index reduction, % | — | 18 | 63 | 57 | 26 |
| Number of animals | 42 | 10 | 36 | 12 | 26 |

*Compared with the control group; the difference at the signifcance level of 95% (at $P < 0.05$)

It can be seen from Table 1 that the proposed hexapeptide given per os, prevented ulceration in the rat duodenum and decreased the ulcer index by 63 percent when given in a dose of 100 μg/kg. The anti-ulcer efficacy of the proposed hexapeptide was higher than that of cimetidine (10 mg/kg) which decreased the ulcer index by 57 percent. The known hexapeptide (U.S. Pat. No. 4,565,805) has only slight anti-ulcer effect when given per os and decreased the ulcer index only by 26 percent.

The proposed hexapeptide was also studied in experiments with indomethacin-induced ulcers of the small intestine. The efficacy of the proposed hexapeptide was compared with that of sulfasalazine. Indomethacin was given to the rats into the stomach through a tube in a dose of 20 mg/kg, in the form of a suspension in 0.5 ml of physiological saline. The proposed hexapeptide or sulfasalazine were given in doses of 100 μg/kg or 200 mg/kg respectively immediately after administration of indomethacin or 6 hours later. Indomethacin was given with 0.5 ml of a 3% milk diluted in 5 volumes of physiological saline. The same amount of the milk solution was given to the control animals. The rats were decapitated in 24 hours after the administration of indomethacin and the number of ulcers on the mucosa of a 30-cm long distal small intestine was counted. (Maximum ulceration was observed in this portion of the intestine). The average number of ulcers was determined for each group of the animals.

The findings were processed statistically using the Student t-criterion. Differences at the significance level of 95 % were taken as trustworthy (at $P<0.05$). The results of the experiments are given in Table 2.

The tabulated date show that the proposed hexapeptide, given in a dose of 100 μg/kg, decreases the average number of ulcers in the distal portion of the small intestine of rats by 52 percent. The anti-ulcer potency of the proposed hexapeptide is not inferior to that of sulfasalazine given in a dose of 200 mg/kg, which decreases the number of ulcers in the intestine by 46 percent.

TABLE 2

Effect of the proposed hexapeptide and sulfasalazine on development of indomethacin-induced ulcers in the small intestine

| Animal group | Number of animals | Average number of ulcers |
|---|---|---|
| Control | 20 | 48.78 ± 6.02 |
| Treated with proposed hexapeptide | 20 | 23.40 ± 5.36* |
| Control | 12 | 50.78 ± 5.81 |
| Treated with sulfasalazine | 12 | 27.50 ± 5.28* |

*The difference compared with the control group is trustworthy at the significance level of 95% (at $P < 0.05$).

No changes in the cell composition of the blood or the main haemodynamic indices were observed in the experiments with the proposed hexapeptide. The $LD_{50}$ of the proposed hexapeptide in acute toxicity tests was 250 mg/kg.

The experiments thus showed that the efficacy of the proposed hexapeptide was not inferior to that of cimetidine (with respect to the duodenum) or sulfasalazine (with respect to the small intestine) in rats with acute erosive and ulcerative lesions of the gastrointestinal tract. But since cimetidine was given in a dose of 10 mg/kg and sulfaselazine in a dose of 200 mg/kg, it follows that the anti-ulcer activity of the proposed hexapeptide in the experiments mentioned was 100 and 2000 times higher than those of cimetidine and sulfasalazine respectively.

The proposed hexapeptide, whose efficacy is higher than that of cimetidine or sulphasalazine is used as the active principle in a medicinal preparation intended to treat ulcer of the stomach, duodenal ulcer, and ulcerative colitis. The advantage of the proposed hexapeptide over cimetidine and sulfasalazine is its higher activity and its possible use for treatment of concurrent erosive lesion of the duodenum and the distal portions of the intestine. Another advantage of the proposed hexapeptide over the known hexapeptide (U.S. Pat. No. 4,565,805) is that it can be given orally.

The proposed medicinal preparation can be used to treat patients with erosive and ulcerative lesions of the gastrointestinal tract in various forms for oral administration of a single dose from 5 to 50 mg.

The proposed medicinal preparation can be given in any form suitable for oral administration, e.g. as powders or tablets, together with milk, vegetable oils or lipids in the dispersed form, as well as in capsules containing any suitable fat carrier. Moreover, the proposed preparation can be administered intranasally as an aerosol or as rectal suppositories.

The prosed hexapeptide with the formula Tyr-D-Ala-Gly-Phe-Leu-Glu is synthesized from two fragments that are obtained by successive build-up of the amino acid chain at one amino acid; di-tert-butyl carbobenzoxy-phenylalanine leucyl-glutamate from di-tert-butyl carbobenzoxy-glutamate; n-tert-butylhydroxycarbonyl-O-benzyl tyrosyl-D-ananyl glycine from the sodium salt of glycine and activated esters of protected amino acids. The fragments were condensed by the activated-ester method after eliminating the carbobenzoxy group. The protective groups were eliminated by catalytic hydrogenolysis and acidolytic cleavage.

The following example is given by way of illustration for a better understanding of the invention.

EXAMPLE 1

6.83 g (17.41 mM) of di-tert-butyl carbobenzoxyglutamate are dissolved in 35 ml of methyl alcohol and hydrated in the presence of palladium 10% on activated charcoal as a catalyst for four hours. The catalyst is then separated on a filter, washed on the filter with methyl alcohol, the filtrate is evaporated and the residue is dissolved in 25 ml of dimethyl formamide. 4.50 g (17.41 mM) of p-nitrophenyl ester of carbobenzoxy leucine are added to the solution and the reaction mixture is stirred at room temperature for 24 hours. The solvent is then evaporated, the residue dissolved in 10 ml of a mixture of ethyl acetate and hexane (2:1) and placed into a chromatographic column with silicagel Si 60 (440×37). Chromatography is carried out in isocratic conditions (the eluent is ethyl acetate and hexane, 2:1). The fractions are evaporated and dried in a vacuum desiccator to obtain 6.02 g (68 percent) of di-tert-butyl carbobenzoxy-leucyl glutamate. This is a colourless oil, =24.2 (with Y, dimethyl formamide), $R_f$: 0.22 (ethyl acetate:n-heptane, 1:2); 0.61 (toluene:acetone:methyl alcohol:acetic acid, 14:1:4:1); 0.50 (toluene:n-heptane:methyl ethyl ketone, 5:3:1).

1.56 g (3.09 mM) of di-tert-butyl carbobenzoxyleucyl glutamate are dissolved in 10 ml of methyl alcohol and hydrated in the presence of a palladium catalyst for 3 hours. The catalyst is then separated on a filter, washed with methyl alcohol, and the filtrate is evaporated. The residue is dissolved in 5 ml of dimethyl formamide, and 1.30 g (3.09 mM) of p-nitrophenyl ester of carbobenzoxyphenylalanide are added. The reaction mixture is stirred at room temperature for 24 hours. The solvent is then evaporated and the residue dissolved in 30 ml of ethyl acetate. The ethyl acetate solution is washed with a 2 percent sulphuric acid solution (20 ml×2), water (20 ml×2), evaporated, then 25 ml of isopropyl alcohol are added and the mixture is evaporated. The residue is dissolved in di-isopropyl ether, the precipitated crystals are separated on a filter, washed with di-isopropyl ether, and dried in a vacuum desiccator. The yield of the process is 1.55 g (85 percent) of di-tert-butyl carbobenzoxyphenylalanine leucyl glutamate, with the melting point at 120° C., $[\zeta]_D^{20} = -25.6°$ (with 1,dimethylformamide); $R_f$:0.23 (ethyl acetate:n-hexane, 1:2), 0.56 (toluene:acetone:methyl alcohol:acetic acid, 14:1:4:1), 0.29 (toluene-n-heptane:methyl ethyl ketone, 5:3:1).

0.50 g (7.68 mM) of glycine are dissolved in 7.68 ml of a 1N sodium hydroxide solution and 2.74 g (7.68 mM) of p-nitrophenyl ester of carbobenzoxy-D-alanine in 20 ml of dimethyl formamide are added. The reaction mixture is stirred at room temperature for 24 hours. The solution is evaporated, the residue dissolved in water and extracted with ether (50 ml×3). The aqueous layer is acidified with a 2N sulphuric acid to pH 2, extracted with ethyl acetate (50 ml×3). The ethyl acetate solution is washed with water (30 ml×2), than 50 ml of isopropyl alcohol are added and the mixture is evaporated. The residue is mixed with 100 ml of ether and the precipitated crystals are separated on a filter, washed with ether on the filter, and dried in a vacuum desiccator.

The yield of the process is 1.40 g (65 percent) of cabobenzoxy-D-alanine glycine melting at 126.5°-127° C.; $[\zeta]_D^{20} = +20.7°$ (with 1, MeOH), $R_f$:0.67 (chloroform:methyl alcohol:32% acetic acid, 60:45:20); 0.71 (ethyl acetate:pyridine:acetic acid:water, 45:20:6:11); 0.35 (methylene chloride:methyl alcohol:50% acetic acid, 85:15:2).

1.66 g (5.90 mM) of carbobenzoxy-D-alaninyl glycine are dissolved in 20 ml of methyl alcohol and hydrate in the presence of a palladium catalyst for 3 hours. The catalyst is separated on a filter, washed with methyl alcohol, the filtrate is dissolved in 5.9 ml of a 1N sodium hydroxide solution; then 2.91 g (5.90 mM) of p-nitrophenyl ester of N-etert-butyloxycarbonyl-O-benzyl-tyrosine in 25 ml of dimethyl formamide are added. The reaction mixture is stirred at room temperature for 24 hours. The solution is then evaporated, the residue dissolved in water and extracted with ether (50 ml×2). The aqueous layer is acidified with a 2N sulphuric acid to pH 2 and extracted with ethyl acetate (70 ml×3). The extract is washed with water (50 ml×2); 50 ml of isopropyl alcohol are added and the mixture is evaporated. The residue is mixed with 150 ml of ether and the precipitated crystals are filtered, washed on the filter with ether and dried in a vacuum desiccator. The yield of the reaction is 2.62 g (89 percent) of N-tert-butyloxycarbonyl-O-benzyl tyrosyl-D-alanine glycine melting at 100°-100.5° C.; $[\zeta]_D^{20} = -9.3°$ (with cl, dimethyl formamide); $R_f$:0.47 (ethyl acetate:pyridine:acetic acid:water, 45:20:6:11); 0.57 (methylene chloride:methyl alcohol:50% acetic acid, 85:15:2); 0.36 (chloroform:methyl alcohol:acetic acid, 9:1:0.5).

3.50 g (7.03 mM) of N-tert-butyloxycarbonyl-O-benzyl-tyrosyl-D-alanine glycine and 1.02 g (7.33 mM) of p-nitrophenol are dissolved in 25 ml of dimethyl-formamide, the solution is cooled to −25° C. and 1.54 g (7.33 mM) of dicyclohexal carbodiimide in 10 ml of dimethyl formamide are added. The reaction mixture is stirred at the temperature of −25° C. for 45 minutes, the temperature is then raised to 0° C. and the mixture is kept at this temperature for 24 hours. The precipitated crystals of dicyclohexylures are separated on a filter, washed with dimethyl formamide, the filtrate is evaporated and the residue is recrystallized from isopropyl alcohol.

The yield is 3.63 g (83 percent) of p-nitrophenyl N-tert-butyloxycarbonyl-O-benzyl-tyrosyl-D-alanyl glycine melting at 154° C.; $[\zeta]_D^{20} = -0.4°$ (with 1,dimethyl formamide); $R_f$:0.87 (methylene chloride:methyl alcohol:50% acetic acid, 85:15:2):0.69 (chloroform:methyl alcohol:acetic acid, 32:2:1); 0.41 (n-butyl alcohol:formic acid:water, 15:3:1).

209 mg (0.32 mM) of di-tert-butyl carbobenzoxyphenylalanyl-leucyl glutamate are dissolved in 15 ml of methyl alcohol and hydrated in the presence of a palladium catalyst for 3 hours. The catalyst is separated on a filter, washed with methyl alcohol and the filtrate is evaporated. The residue is dissolved in 10 ml of dimethyl formamide and 200 mg of p-nitrophenyl N-tert-butoxycarbonyl-O-benzyl-tyrosyl-D-analyl glycine are added. The reaction mixture is stirred at room temperature for 24 hours, dimethylformamide removed by evaporation and the residue is reprecipitated from methyl alcohol (5 ml) two times using ether (300 ml). The yield of the reaction is 266 mg (84 percent) of di-tert-butyl N-tert-butyloxycarbonyl-O-benzyl-tyrosyl-D-alanyl-glycyl-phenylanalyl-leucyl glutamate melting at 200°-201° C.; $[\zeta]_D^{20} = -19.2°$ (with 1, dimethylformamide); $R_f$:0.88 (chloroform:methyl alcohol:32% acetic acid, 60:45:20); 0.89 (ethyl acetate: pyridine;acetic acid:water,45:20:6:11); 0.58 (chloroform: methyl alcohol:acetic acid, 9:1:0.5).

240 mg (0.24 mM) of di-tert-butyl N-tert-butyloxycarbonyl-O-benzyl-tyrosyl-D-alanyl-glycylphenylanalyl-leucyl glutamate are dissolved in 15 ml of acetic acid and hydrated in the presence of palladium for 3 hours. The catalyst is separated on a filter, washed on the filter with acetic acid, and the filtrate is evaporated. The residue is dissolved in 15 ml of trifluoroacetic acid and kept at room temperature for 30 minutes. The solution is then evaporated, mixed with 50 ml of ether, and the precipitated substance is separated on a filter, washed with ether, dissolved in 50 ml of a 10 percent acetic acid, and treated with the ion exchange resin Dowex-1 in the AcO$^-$ form. The resin is then separated on a filter, washed with a 10 percent acetic acid and the filtrate is evaporated. The obtained produce is purified by centrifuging by the countercurrent distribution method (planet centrifuge) in the system n-butyl alcohol:acetic acid:water, 4:1:5; the stationary phase is organic. The fractions containing the end product are collected and evaporated. The residue is reprecipitated from methyl alcohol (3 ml) with ether (250 ml). The precipitate is filtered, washed on the filter with ether, and dried in a vacuum desiccator.

The yield is 92 mg (55 percent) tyrosyl-D-ananyl-glycyl-phenylalanylleucyl glutamate; $[\zeta]_D^{20} = 29.8°$ C. (with 1, 10% AcOH); $R_f$ 0.47 (chloroform: methyl alcohol: 32% acetic acid, 60:45:20); 0.42 (ethyl acetate: pyridine:acetic acid:water, 45:20:6:11); 0.48 (n-butyl alcohol:acetic acid:water, 3:1:1). Amino acid essay: alanine 1.02 (1), glycine 1.00(1), glutamic acid 1.04 (1), leucine 1.02 (1), tyrosyl 0.99 (1), phenylalanine 1.03(1). The findings of high-performance liquid chromatography: the peptide was eluted with one peak at 38.24 percent gradient at 12, 16 minutes; the column size, 250×4.6 mm, Ultrasphere ODS, 5 m; the mobile phase A: 0.05M $KH_2PO_4$, B: $CH_3CN$ gradient 20→50 percent B for 20 min; pressure 1500 psi; the rate, 1 ml/min; detection at 214 nm.

INDUSTRIAL APPLICABILITY

The herein-proposed hexapeptide displays an antiulcerative effect and may find application in medicine as an active principle in a medicinal preparation for treating erosive and ulcerative lesions of the gastrointestinal tract.

What is claimed is:

1. A hexapeptide having the structure Tyr-D-Ala-Gly-Phe-Leu-Glu.

2. A medicinal preparation for treating erosive and ulcerative lesions of the gastrointestinal tract comprising an active principle and a pharmaceutical carrier wherein it comprises as the active principle, the hexapeptide as claimed in claim 1.

3. A medicinal preparation as claimed in claim 2, which contains the active principle in a single dose in the quantity of 5 to 50 mg.

4. A medicinal preparation as claimed in claim 2, in the form of capsules, which contains the active principle in the quantity of 5 to 50 mg in one capsule.

5. A medicinal preparation as claimed in claim 4, which comprises olive oil as the pharmaceutical carrier.

* * * * *